(12) United States Patent
Bogdanov

(10) Patent No.: US 9,095,625 B2
(45) Date of Patent: Aug. 4, 2015

(54) GRAFT-COPOLYMER STABILIZED METAL NANOPARTICLES

(71) Applicant: University of Massachusetts, Boston, MA (US)

(72) Inventor: Alexei A. Bogdanov, Westborough, MA (US)

(73) Assignee: University of Massachusetts, Boston, MA (US)

( * ) Notice: Subject to any disclaimer, the term of this patent is extended or adjusted under 35 U.S.C. 154(b) by 22 days.

(21) Appl. No.: 13/826,064

(22) Filed: Mar. 14, 2013

(65) Prior Publication Data

US 2014/0065425 A1  Mar. 6, 2014

Related U.S. Application Data

(60) Provisional application No. 61/695,576, filed on Aug. 31, 2012.

(51) Int. Cl.
*A61K 47/48* (2006.01)

(52) U.S. Cl.
CPC ..... *A61K 47/48315* (2013.01); *A61K 47/48884* (2013.01); *Y10T 428/2998* (2015.01)

(58) Field of Classification Search
CPC .............. A61K 47/48315; A61K 47/48884; Y10T 428/2998
USPC .................................. 428/403, 407; 525/54.1
See application file for complete search history.

(56) References Cited

U.S. PATENT DOCUMENTS

| | | | |
|---|---|---|---|
| 7,229,841 B2 * | 6/2007 | Tamarkin et al. | 436/525 |
| 7,586,033 B2 | 9/2009 | Ren et al. | |
| 7,718,094 B2 * | 5/2010 | Alexandridis et al. | 252/514 |
| 8,206,747 B2 | 6/2012 | Zale et al. | |
| 8,754,062 B2 * | 6/2014 | de Fougerolles et al. | 514/44 R |
| 8,865,796 B2 * | 10/2014 | Benicewicz et al. | 523/202 |
| 2005/0175584 A1 | 8/2005 | Paciotti et al. | |
| 2007/0031327 A1 | 2/2007 | Luzzi et al. | |
| 2008/0226562 A1 | 9/2008 | Groves et al. | |
| 2009/0298676 A1 | 12/2009 | Meier et al. | |
| 2010/0172997 A1 | 7/2010 | Omary et al. | |
| 2010/0298925 A1 | 11/2010 | Thomas et al. | |
| 2010/0330368 A1 | 12/2010 | Prud'homme et al. | |
| 2011/0250284 A1 | 10/2011 | Lavik et al. | |
| 2012/0014874 A1 | 1/2012 | Choi et al. | |

OTHER PUBLICATIONS

Sun et al, : "Tumor-targeting Gold Particles . . . " Angew. Chem. Int. Ed. 2011. 50, 9348-9351.*

Arima et al., Complement activation on surfaces modified with ethylene glycol units. Biomaterials. Feb. 2008; 29(5):551-60. Epub Nov. 5, 2007.

Banerjee et al., Linear polyethyleneimine grafted to a hyperbranched poly(ethylene glycol)-like core: a copolymer for gene delivery. Bioconjug Chem. Jan.-Feb. 2006;17(1):125-31.

Benesch et al., Blood protein adsorption onto chitosan. Biomaterials. Jun. 2002;23(12):2561-8.

Bertholon et al., Complement activation by core-shell poly(isobutylcyanoacrylate)-polysaccharide nanoparticles: influences of surface morphology, length, and type of polysaccharide. Pharm Res. Jun. 2006;23(6):1313-23. Epub May 25, 2006.

Bogdanov et al., A new macromolecule as a contrast agent for MR angiography: preparation, properties, and animal studies. Radiology. Jun. 1993;187(3):701-6.

Bogdanov et al., An adduct of cis-diamminedichloroplatinum(II) and poly(ethylene glycol)poly(L-lysine)-succinate: synthesis and cytotoxic properties. Bioconjug Chem. Jan.-Feb. 1996;7(1):144-9.

Bogdanov et al., A long-circulating co-polymer in "passive targeting" to solid tumors. J Drug Target. 1997;4(5):321-30.

Bogdanov et al., Protected Graft Copolymer (PGC) in Imaging and Therapy: A Platform for the Delivery of Covalently and Non-Covalently Bound Drugs. Theranostics. 2012;2(6):553-76. doi: 10.7150/thno.4070. Epub Jun. 4, 2012.

Bogdanov et al., Soft-matter meets condensed matter: synthesis and in vivo testing of long-circulating biocompatible stable gold nanoparticles. University of Massachusetts Medical School. Poster Session Presentation. Sep. 5, 2012. 22 pages and table of contents.

Brown et al., Colloidal metallic gold is not bio-inert. Inflammopharmacology. Jun. 2008;16(3):133-7. doi: 10.1007/s10787-007-0017-6.

Butterworth et al., Evaluation of cytotoxicity and radiation enhancement using 1.9 nm gold particles: potential application for cancer therapy. Nanotechnology. Jul. 23, 2010;21(29):295101. doi: 10.1088/0957-4484/21/29/295101. Epub Jul. 5, 2010.

Callahan et al., Preclinical evaluation and phase I clinical trial of a 99mTc-labeled synthetic polymer used in blood pool imaging. AJR Am J Roentgenol. Jul. 1998;171(1):137-43.

Cherukuri et al., Targeted hyperthermia using metal nanoparticles. Adv Drug Deliv Rev. Mar. 8, 2010;62(3):339-45. doi: 10.1016/j.addr.2009.11.006. Epub Nov. 10, 2009.

Chithrani et al., Gold nanoparticles as radiation sensitizers in cancer therapy. Radiat Res. Jun. 2010;173(6):719-28. doi: 10.1667/RR1984.1.

Dumur et al., Controlled spontaneous generation of gold nanoparticles assisted by dual reducing and capping agents. Gold Bull. 2011;44:119-137.

(Continued)

*Primary Examiner* — Leszek Kiliman
(74) *Attorney, Agent, or Firm* — Nutter McClennen & Fish LLP; John J. Penny, Jr.; Isaac A. Hubner

(57) ABSTRACT

There is provided a method of preparing nanoparticles and novel nanoparticles. The nanoparticle preparation comprises the generation of a mixture comprising a plurality of metal-containing compounds and a copolymer of a polyethylene glycol and an amine-containing polyamino acid such as polylysine where a metal core and polymer shell nanoparticle is formed. The novel nanoparticles have a metallic core and a graft copolymer shell of polyethylene glycol and an amine-containing polyamino acid where the shell least partially surrounds the metallic core and is non-ionically bound to the metallic core via metal-amine bonds.

19 Claims, 7 Drawing Sheets

(56) References Cited

OTHER PUBLICATIONS

Ge et al., A simple colorimetric detection of DNA methylation. Analyst. May 7, 2012;137(9):2032-5. doi: 10.1039/c2an35043b. Epub Mar. 16, 2012.

Hainfeld et al., Gold nanoparticles enhance the radiation therapy of a murine squamous cell carcinoma. Phys Med Biol. Jun. 7, 2010;55(11):3045-59. doi: 10.1088/0031-9155/55/11/004. Epub May 12, 2010.

Heo et al., Gold nanoparticles surface-functionalized with paclitaxel drug and biotin receptor as theranostic agents for cancer therapy. Biomaterials. Jan. 2012;33(3):856-66. doi: 10.1016/j.biomaterials.2011.09.064. Epub Oct. 27, 2011.

Ishii et al., Preparation of functionally Pegylated gold nanoparticles with narrow distribution through autoreduction of auric cation by alpha-biotinyl-PEG-block-[poly(2-(N,N-dimethylamino)ethyl methacrylate)]. Langmuir. Feb. 3, 2004;20(3):561-4.

Lin et al., Gold nanoparticle probes for the detection of mercury, lead and copper ions. Analyst. Mar. 7, 2011; 136(5):863-71. doi: 10.1039/c0an00652a. Epub Dec. 15, 2010.

Mackiewicz et al., C-reactive protein induced rearrangement of phosphatidylcholine on nanoparticle mimics of lipoprotein particles. J Phys Chem B. Apr. 29, 2010;114(16):5556-62. doi: 10.1021/jp911617q.

Marchand et al., C3, C5, and factor B bind to chitosan without complement activation. J Biomed Mater Res A. Jun. 15, 2010;93(4):1429-41. doi: 10.1002/jbm.a.32638.

Miron et al., A simplified method for the preparation of succinimidyl carbonate polyethylene glycol for coupling to proteins. Bioconjug Chem. Nov.-Dec. 1993;4(6):568-9.

Nusz et al., Rational selection of gold nanorod geometry for label-free plasmonic biosensors. ACS Nano. Apr. 28, 2009;3(4):795-806. doi: 10.1021/nn8006465.

Okada et al., New protein purification system using gold-magnetic beads and a novel peptide tag, "the methionine tag". Bioconjug Chem. May 18, 2011;22(5):887-93. doi: 10.1021/bc100429d. Epub Apr. 13, 2011.

Rasmussen et al., Covalent immobilization of DNA onto polystyrene microwells: the molecules are only bound at the 5' end. Anal Biochem. Oct. 1991;198(1):138-42.

Sakai et al., Mechanism of gold metal ion reduction, nanoparticle growth and size control in aqueous amphiphilic block copolymer solutions at ambient conditions. J Phys Chem B. Apr. 28, 2005;109(16):7766-77.

Sherman et al., Role of the methoxy group in immune responses to mPEG-protein conjugates. Bioconjug Chem. Mar. 21, 2012;23(3):485-99. doi: 10.1021/bc200551b. Epub Mar. 7, 2012.

Simpson et al., Unexpected toxicity of monolayer protected gold clusters eliminated by PEG-thiol place exchange reactions. Chem Res Toxicol. Oct. 18, 2010;23(10):1608-16. doi: 10.1021/tx100209t. Epub Jul. 22, 2010.

Song et al., Gold nanoparticles capped with polyethyleneimine for enhanced siRNA delivery. Small. Jan. 2010; 6(2):239-46. doi: 10.1002/smll.200901513.

Sun et al., Tumor-targeting gold particles for dual computed tomography/optical cancer imaging. Angew Chem Int Ed Engl. Sep. 26, 2011;50(40):9348-51. doi: 10.1002/anie.201102892. Epub Aug. 26, 2011.

Szott et al., Complement activation on poly(ethylene oxide)-like radiofrequency glow discharge-deposited surfaces. J Biomed Mater Res A. Jan. 2011;96(1):150-61. doi: 10.1002/jbm.a.32954. Epub Nov. 5, 2010.

Wang et al., An improved synthesis of NHS-MAG3 for conjugation and radiolabeling of biomolecules with (99m)Tc at room temperature. Nat Protoc. 2007;2(4):972-8.

Winnard et al., Preparation and use of NHS-MAG3 for technetium-99m labeling of DNA. Nucl Med Biol. Jul. 1997; 24(5):425-32.

Yarom et al., Nephrotoxic effect of parenteral and intraarticular gold. Ultrastructure and electron microprobe examination of clinical and experimental material. Arch Pathol. Jan. 1975;99(1):36-42. Abstract.

Yoon et al., Application of near-infrared fluorescence imaging using a polymeric nanoparticle-based probe for the diagnosis and therapeutic monitoring of colon cancer. Dig Dis Sci. Oct. 2011;56(10):3005-13. doi: 10.1007/s10620-011-1685-z. Epub Apr. 5, 2011.

Zheng et al., Ethylene glycol monolayer protected nanoparticles for eliminating nonspecific binding with biological molecules. J Am Chem Soc. Jul. 2, 2003;125(26):7790-1.

Zijlstra et al., Optical detection of single non-absorbing molecules using the surface plasmon resonance of a gold nanorod. Nat Nanotechnol. Apr. 15, 2012;7(6):379-82. doi: 10.1038/nnano.2012.51.

* cited by examiner

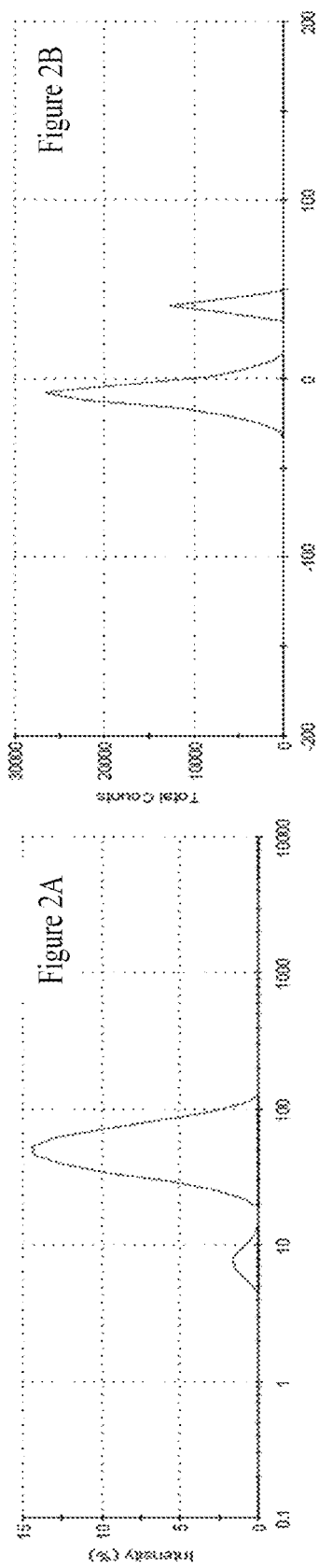
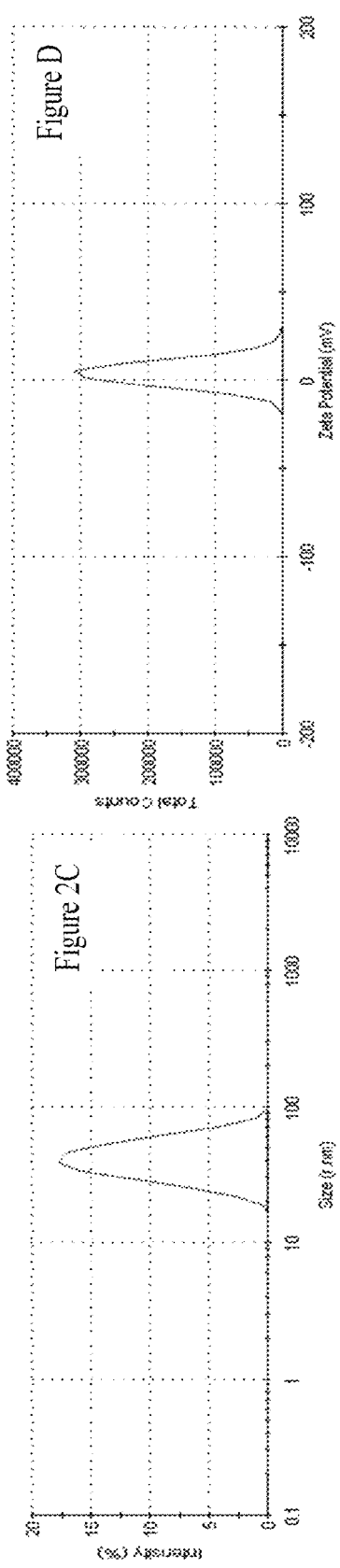

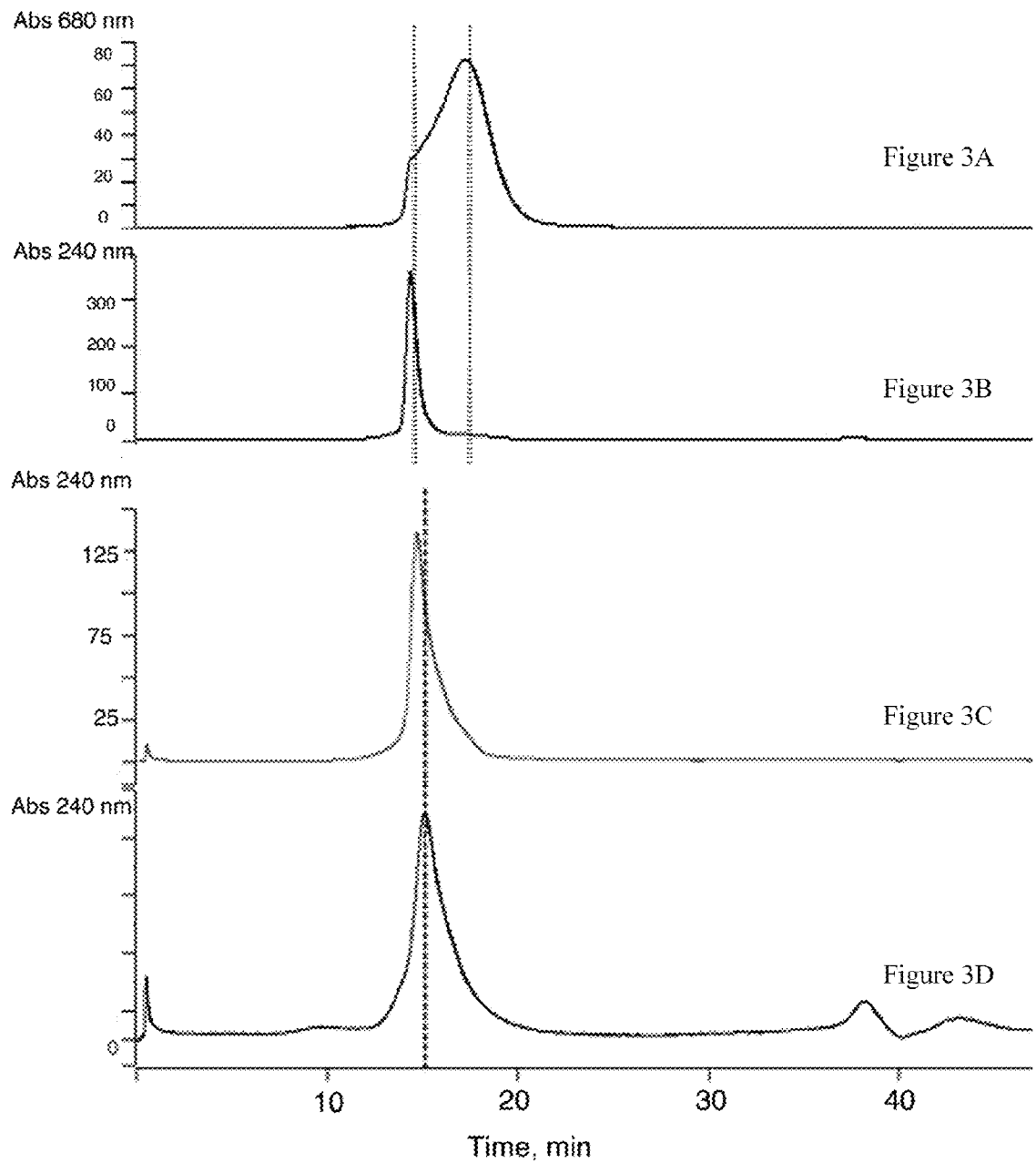

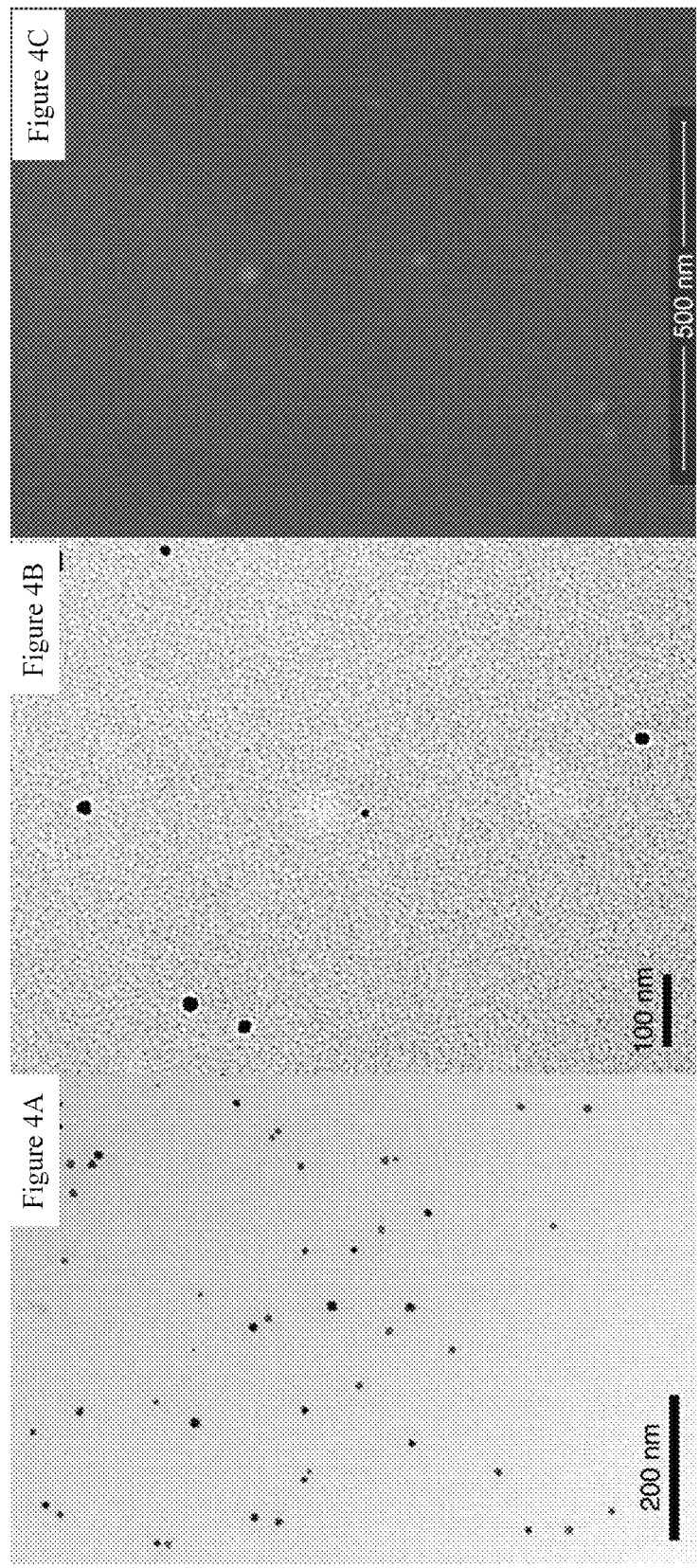

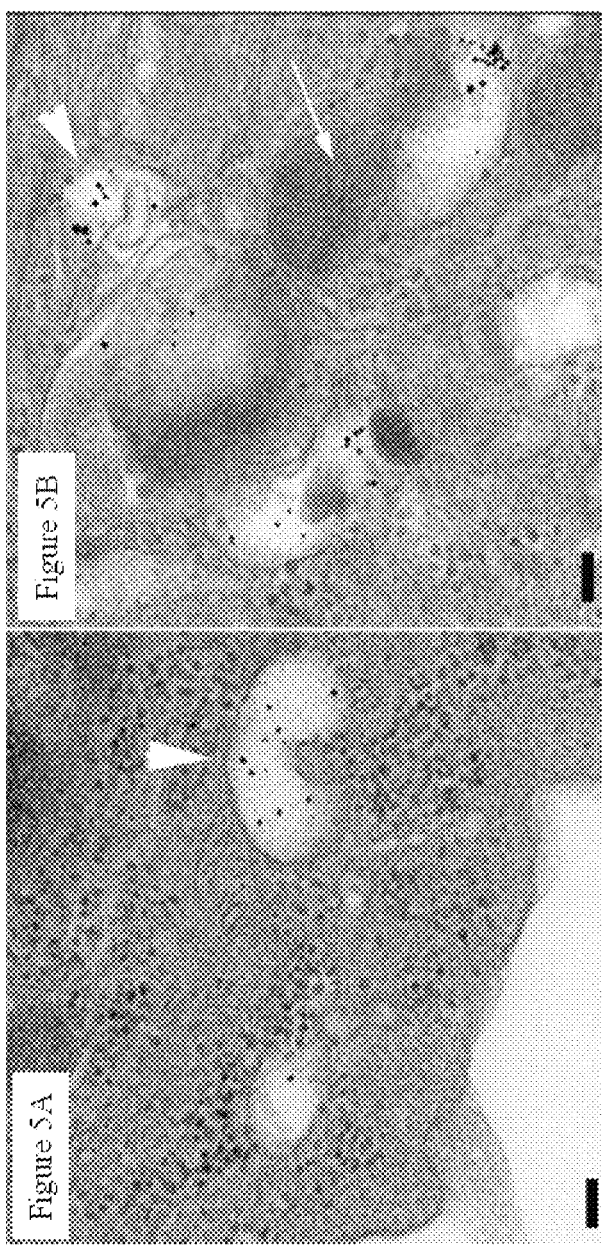
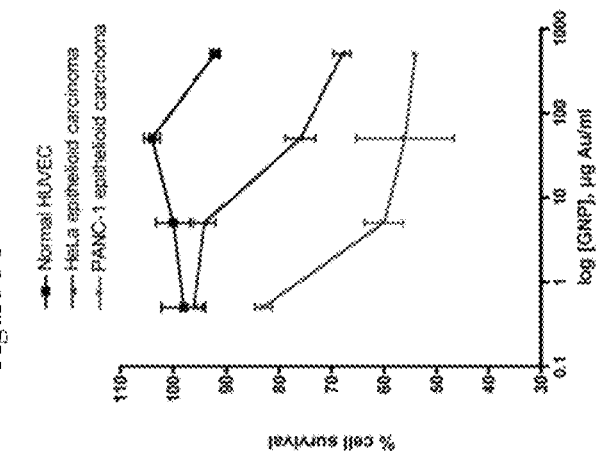

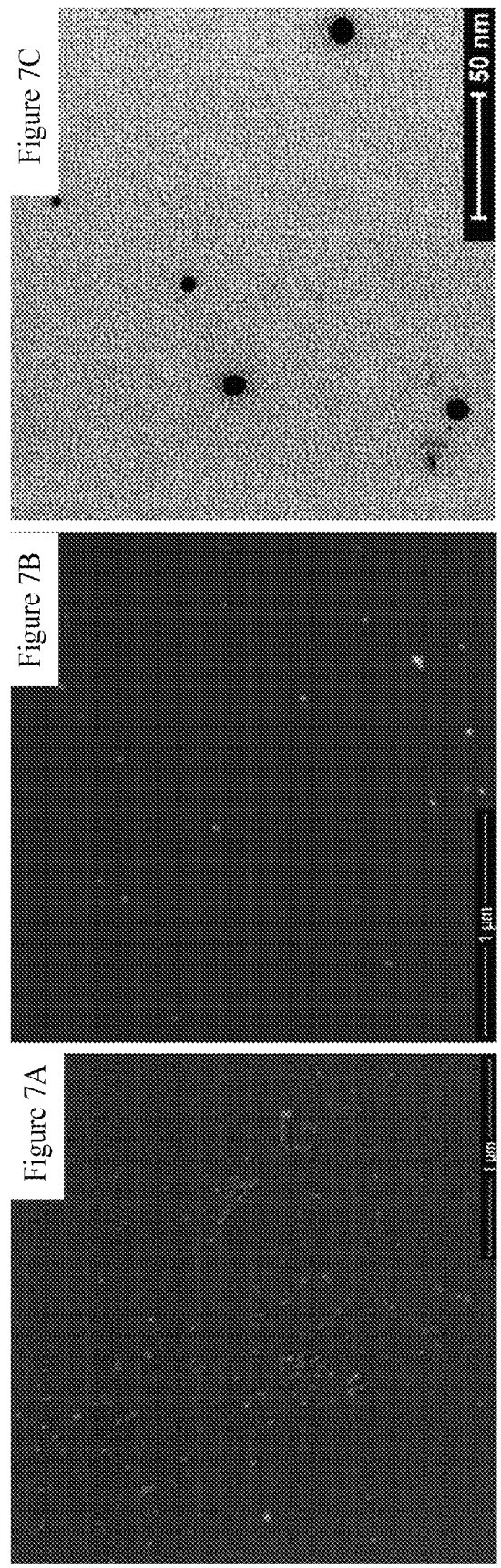

GRAFT-COPOLYMER STABILIZED METAL NANOPARTICLES

CROSS-REFERENCE TO RELATED APPLICATIONS

This application claims priority to U.S. Provisional Application No. 61/695,576 filed Aug. 31, 2012, which is herein incorporated by reference in its entirety.

STATEMENT REGARDING FEDERALLY SPONSORED RESEARCH

This invention was made with government support under grant no. EB000858 awarded by the National institutes of Health. The government has certain rights in the invention.

FIELD OF THE INVENTION

The present invention relates generally to the fields of material science, drug delivery and imaging applications in medicine. In particular, the invention relates to biocompatible metallic nanoparticles, their synthesis, and their use.

BACKGROUND

Gold nanoparticles (GNPs), commonly known as colloidal gold, find an increasing number of potential biomedical applications, both in diagnostics and therapy of disease. The unique opto-electrical properties of GNPs, which can be defined by the presence of metallic cores and surface plasmons, have promoted wide use of GNPs in diagnostics. The spectral changes resulting from the particle size change or particle aggregation of the GNPs can be useful in designing systems for molecular recognition of biomolecules. In some applications, GNPs can be used as individual nano-sensors. Such nano-sensors can rely on binding of molecules to the GNPs surfaces and resultant plasmonic interactions for sensing changes in the environment.

However, there are significant problems with GNPs. Gold is not bio-inert, and mild-to-severe nephrotoxicity of gold-containing preparations have been found in various animals in the past. Bare GNPs present in a solution are typically unstable and will aggregate and precipitate out of the solution. Gold and silver/gold nanoparticles form stable colloidal suspensions in water only in the presence of a special stabilizer or a stabilizer with reducing properties that can be added during the synthesis of metallic nanoparticles. The most commonly used stabilizer/reducer is sodium citrate. Such colloidal suspensions collapse at high nanoparticle concentrations in the presence of sodium citrate. To prevent such colloidal solutions from becoming unstable, polymers (linear, diblock, triblock, or dendrimeric) have been used to coat the already-formed nanoparticles. The precursor metallic nanoparticles are usually obtained by using sodium citrate (Turkevich's method), which acts as a reducing/capping reagent. Another method for producing metallic nanoparticles (Martin's method, as well as similar but more complex Brust's methods) requires the use of sodium borohydride as a reducer and 1-dodecanethiol as a stabilizer. In the latter case, extraction into organic phase is required. However, the need in a long-chain aliphatic thiol stabilizer severely limits the ability to add new or several functionalities to the surface of the nanoparticles. Additionally, the use of such compounds can require an additional derivatization step in the synthesis of the GNPs.

It is generally believed that a combination of small particle size and a protective layer on the surface of GNPs improves their biocompatibility. The latter is usually provided by adsorbing and/or chemically orienting polymers [23] on the surface of nanoparticles generating a layer that is sterically and chemically protective. There are prior water-based GNP synthesis strategies that utilize a combination of reducing/gold colloid capping polymers leading to GNP preparations of various diameters, and a variety of surface properties [24]. Of these polymers, very few provide a stable and relatively biologically inert coating, which is required for the GNPs to escape recognition and sequestration by macrophages [25]. A high molecular weight deacetylated chitosan has been recently suggested as a potential replacement for more commonly used protective polymer PEG-thiol [26, 27]. Though the use of the latter does result in stabilized and relatively biologically inert nanoparticles [28], unlike chistosan, PEG-coated GNPs are unstable in the presence of reduced glutathione [27, 29]. However, unlike chitosan, [30-32] methoxypoly(ethylene glycol) does not bind, nor does it activate, complement components unless terminal hydroxyl is exposed on PEG chains [33].

Thus, novel nanoparticles and methods of preparing such nanoparticles that overcome these and other problems associated with conventional nanoparticles and synthesis methods are needed.

SUMMARY

In accordance with certain embodiments of the present invention, a method of preparing a plurality of nanoparticles is disclosed, which comprises generating a mixture comprising a plurality of metal-containing compounds and a copolymer of a polyethylene glycol and at least one primary amino group-containing polyamino acid so as to cause a reaction between the copolymer and said metal-containing compounds, thereby reducing at least a fraction of metal included in the composition of metal-containing compounds to a lower oxidation state, wherein said reduced metals facilitate (or result in) a formation of a plurality of nanoparticles having a single or a composite metallic core and a coating of said copolymer, and wherein said mixture lacks a reducing agent having a thiol moiety. In some embodiments, the metal-containing compounds are metal ions. In some embodiments, the method further comprises maintaining said mixture at temperatures in a range of between about 4° C. and 99° C. The temperate may be an elevated temperature in a range of about 90° C. and 99° C. in the presence of a reducer, which may be chosen from group of citric acid salts or bis(carboxymethyl)lysine salts, added to the said mixture.

In some embodiments, the mixture of the metal-containing compounds and the copolymer may be formed by combining an aqueous solution comprising the metal-containing compounds with a solution comprising the copolymer. The plurality of metal-containing compounds may be formed by adding a metal salt, such as gold (III) chloride, to water. The metal-containing compounds may comprise any of gold, gold and silver; gold and platinum; gold, and silver and platinum ions. In some embodiments in which two or three different metal-containing compounds are present in the mixture, it is preferred to have at least twice as many gold ions as silver and/or platinum ions.

In some embodiments, at least a portion of the said mixture of the metal-containing compounds and the copolymer is comprised of metallic and metal oxide nanoparticles, such as silver, Fe(II) and Fe(III) oxide or a combination thereof. The metallic and metal oxide nanoparticles may be stabilized and prevented from aggregation with a plurality of carbon-containing polymers.

In some embodiments, the carbon-containing polymers are chosen from a group of dextran, carboxymethyl dextran, ficoll, mannan which may form bonds with amine-containing polyamino acids.

In some embodiments, polyethylene glycol comprises about 90-95% of the copolymer and said amine-containing polyamino acid comprises about 5-10% of the copolymer. In some embodiments, the amine-containing polyamino acid is any of poly-L-lysine and poly-D-lysine. The copolymer may be acylated at the N-ϵ-amino group, where, in some embodiments, approximately 10%-20% of the copolymer N-ϵ-amino groups are acylated. In some embodiments, the polyethylene glycol is a methoxy polyethylene glycol (MPEG) or derivative thereof. Preferably, the copolymer coating covers at least about 50 percent of said metallic core.

In some embodiments, the method of preparing nanoparticles may further comprise reducing the elevated temperature, e.g., by placing the reaction mixture into an ice bath, to quench the reaction between the metal-containing compounds and the copolymer. The method may also involve a purification step, such as centrifugation using a cushion comprising a non-ionic contrast agent. While in many embodiments the copolymer can be sufficient to provide nucleation and aggregation of the metal-containing compounds, in some embodiments, it is preferable to include an additional reducing agent such as a trisodium citrate to the reaction mixture.

In some embodiments, the plurality of nanoparticles is formed at a concentration of at least about 0.005% of the metal-containing compounds.

In some aspect, the invention also provides a nanoparticle, which comprises a metallic core, and a copolymer shell of a polyethylene glycol and an amine-containing polyamino acid that at least partially surrounds the metallic core, wherein said copolymer shell is non-ionically bound to the metallic core via metal-amine bonds. In other embodiments, the copolymer shell covers at least about 50 percent, about 75 percent, about 80 percent, or about 90 percent, or 100 percent, of said metallic core.

In some embodiments, at least about 50 percent of the copolymers in said shell are non-ionically bound to the metallic core via metal-amine bond.

Preferably, the nanoparticle is a stable and non-aggregating nanoparticle, which has a Zeta potential of between about −14 and +10 mV. In some embodiments, the metallic core is about 5-25 nm in diameter and the nanoparticle has a hydrodynamic diameter of about 10-100 nm. The composition in the graft copolymer shell may include a polyethylene glycol comprising about 90-95% of the copolymer and an amine-containing polyamino acid comprising about 5-10% of the copolymer.

In some embodiments, the metallic core comprises gold. It may also comprise gold and one or more of platinum and silver. In some embodiments, the amine-containing polyamino acid is poly-L-lysine, poly-D-lysine, or a combination thereof. The poly lysine may be acylated at the N-ϵ-amino moiety such that approximately 10-20% of the copolymers N-ϵ-amino groups are acylated. In some embodiments, the polyethylene glycol is a methoxy polyethylene glycol (MPEG) or derivative thereof such as an N-hydroxysuccinimide ester, an imidazolide, a pentafluorophenyl ester, or an ethylthioacetate of MPEG or said derivative is O-Methyl (PEG))-O'-succinate. In some embodiments, the copolymer has the structure:

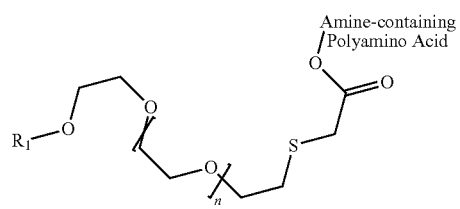

wherein $R_1$ is hydrogen, a lower alkyl, or a protecting group and n is 20-220.

In some embodiments, the nanoparticles according to the present teachings can be particularly useful as therapeutic or imaging agents. For example, the nanoparticles can include an imaging or therapeutic moiety non-ionically or ionically attached to the copolymer, such as to an N-ϵ-amino moiety. In some embodiments, the imaging moiety is an IR dye. In some embodiments, the therapeutic moiety is a short negatively charged oligonucleotide or oligonucleotide duplex.

These and other features of the embodiments as will be apparent are set forth and described herein.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

FIG. 1A—Absorbance spectra showing the positions and intensities of the Plasmon peak. FIG. 1B—An image of a PCR plate well contents after the synthesis of GNPs according to an embodiment of the present teachings, in a plate format. High concentration of HAuCl₄ (160 μM) required concentrations of MPEG-gPLL higher than 0.15 mg/ml.

FIGS. 2A-2D. Z-average hydrodynamic diameter (LALLS intensity (FIGS. 2A and 2C) and zeta potential (charge) of GNPs according to an embodiment of the present teachings, before (FIGS. 2A and 2B) and after (FIGS. 2C and 2D) purification.

FIGS. 3A-3D. Size-exclusion Superdex200 HPLC elution profiles of IR Dye 6804 labeled and semi-purified GNP3 according to an embodiment of the present teachings, (FIGS. 3A and 3B) FIG. 3A—absorbance at 680 nm, FIG. 3B—absorbance 240 nm; FIG. 3C—HPLC of non-modified purified GNP3 and FIG. 3D—MPEG-gPLL with non-cleavable MPEG chains (compound (2)).

FIGS. 4A-4C. Electron microscopy of GNP3 according to an embodiment of the present teachings. FIG. 4A—low magnification TEM; FIG. 4B—high magnification TEM; FIG. 4C—scanning electron microscopy of adsorbed GNP.

FIGS. 5A-5C. The uptake of GNP3 according to an embodiment of the present teachings, in PANC-1 cells. FIG. 5A—the presence of individual GNP3s in the endosomes (arrowhead); FIG. 5B—the fusion of endosome (arrowhead) with the lysosomes (arrow); FIG. 5C—gold concentration dependent cytotoxicity measured in cell culture of the normal HUVEC (black); HeLa cells (blue); and PANC-1 cells (red).

FIG. 6A—the SPECT image fused with CT image acquired 20 min after injecting a total dose of 500 μCi of 99 mTc-labeled GNP3; FIG. 6B—image acquired 22 h after injecting the nanoparticles. The area of GNP3 interstitial leakage is shown by an arrow.

FIGS. 7A-7C. Scanning electron microscopy and back-scatter image of iron oxide nanoparticles used to synthesize gold-silver-iron oxide nanoparticles (FIG. 7B). The latter are shown at high resolution in transmission electron microscopy image (FIG. 7C). These nanoparticles carry electron-dense corona. Unlike initial iron oxide nanoparticles (FIG. 7A), gold-silver-iron oxide nanoparticles (B) exhibit very high back-scatter of X-rays consistent with the presence of gold.

Figure 1A:
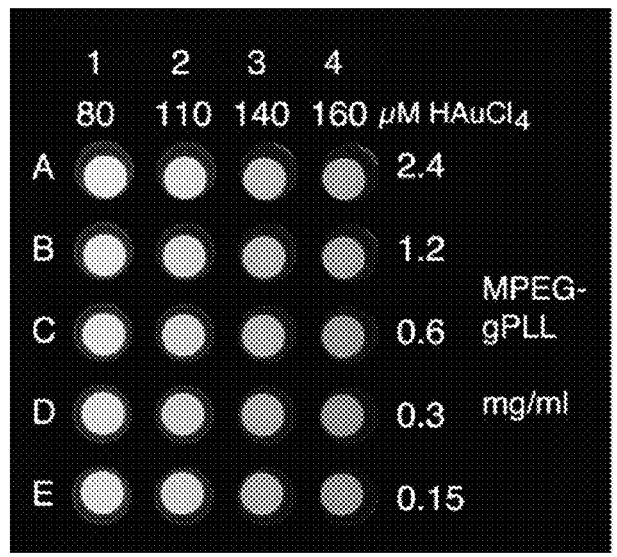
FIGS. 1A and 1B.

It will be understood that the drawings are exemplary only and that all reference to the drawings is made for the purpose of illustration only, and is not intended to limit the scope of the embodiments described herein below in any way.

DETAILED DESCRIPTION

The present disclosure is directed to metal nanoparticles, their synthesis and use. The term "nanoparticle" is used herein to refer to a material structure whose size in any dimension (e.g., x, y, and z Cartesian dimensions) is less than about 1 micrometer (micron), e.g., less than about 500 nm or less than about 200 nm or less than about 100 nm, and greater than about 5 nm. A nanoparticle can have a variety of geometrical shapes, e.g., spherical, ellipsoidal, etc. In various embodiments, for example, the nanoparticle can be a rod, sphere, or any other three dimensional shape.

The "amine-containing polyamino acids," as the term is used herein, include the polyamino acids having one or more amine on the amino acid side chain. This includes polyamino acids of the natural amino acids such as lysine and glutamine as well as arginine, tryptophan and histidine. Preferably, the amine-containing polyamino acid is polylysine.

The term "covalent bond" refers to a chemical bond that involves sharing a pair of electrons between atoms.

The phrases "hydrodynamic diameter" and "hydrodynamic size" refer to the diameter of a putative spherical particle that would have a diffusion coefficient equal to that of the nanoparticle as measured by dynamic light scattering (DLS). Hydrodynamic diameter values may vary depending on the medium in which the agent being measured is dispersed. Thus, unless otherwise indicated, the hydrodynamic diameter values described herein were measured using DLS where the agent is dispersed in 1 mM sodium phosphate, 15 mM sodium chloride, pH 7.5.

An elevated temperature, as described herein, is a temperature above room temperature. The use of an elevated temperature can facilitate the reaction. In one embodiment, the elevated temperature is above 80° C. and up to a temperature required for a rolling boil. In one embodiment the elevated temperature is a temperature in the range of about 90° C. to about 99° C.

As used herein, the term "lower alkyl" refers to both straight and branched chain hydrocarbon groups containing from one to six carbon atoms such as methyl, ethyl, propyl, isopropyl, etc.

The term "metallic core," as used herein refers to a central structure of the nanoparticle, which is formed primarily of a metal. For example, in some embodiments, at least about 70%, or at least about 80%, or at least about 90%, and in some cases 100% of the core is formed of a metal. In some embodiments, the core may include non-metal impurities.

In some embodiments, a variety of metal compounds can be used to form a solution comprising metal ions. Non-limiting examples of such metals include main group metals such as, e.g., lead, tin, antimony and indium, and transition metals such as, e.g., gold, silver, copper, nickel, cobalt, palladium, platinum, iridium, osmium, rhodium, ruthenium, rhenium, vanadium, chromium, manganese, niobium, molybdenum, tungsten, tantalum, iron and cadmium. Examples of preferred metals include gold, silver, platinum, copper and nickel. Examples of metal salts include those of gold ($HAuCl_4$ chloroauric acid) and platinum (tetrachloroplatinate(II) and diamminedicholoplatinate(II)).

In some embodiments, the metal core can include combinations of two or more metals. For example, the metal core can be a combination of both metallic and metal oxide nanoparticles, where the metal may be, for example a main group metal and the metal oxide may be, for example, an iron oxide such as Fe(II) and Fe(III) oxides or a combination thereof.

In some such embodiments in which gold is one of the metals, the concentration of the gold is at least twice that of the other metals In some embodiments, the gold concentration is at least about 50%, 60%, 70%, 80%, 90%, or 95% of a di- or tri-metal nanoparticle in which gold is one of the metals. The metallic core may, for example, have a diameter of about 3-100 nm, or about 3-50 nm or more particularly about 5-25 nm.

As used herein, the term "mixture" includes solutions and suspensions, such as colloidal suspensions and emulsions. The term "solution" is intended to mean substantially homogeneous mixtures that are substantially clear and free of suspended particulates.

As used herein, the phrases "non-aggregating nanoparticle" and "non-aggregated nanoparticle" means that the nanoparticles are substantially free of aggregated nanoparticles, which refer to clusters or clumps of nanoparticles that are firmly associated with one another and that can typically only be separated with high shear. In some embodiments, less than about 2 weight percent, less than about 1 weight percent, less than about 0.5 weight percent, or less than about 0.2 weight percent of the nanoparticles are aggregated. Preferably, the non-aggregated nanoparticles will remain non-aggregated when challenged with moderate changes, for example, in pH.

As used herein the terms "zeta potential," "surface potential," and the abbreviation "ζ" refers to a measurement of the electrostatic potential near the surface of the particle. As the zeta potential is affected by the solvent and ionic strength of the solvent, all zeta potential values reported herein are measured using 1 mM sodium phosphate, pH 7.0 as the solvent unless otherwise indicated. In some embodiments the nanoparticles have a zeta potential in the range of about −14 to about +10 mV or in the range of about −14 to about +6 mV, or in the range of about −12 to about +4 mV, or in the range of about −8 to about +4 mV.

In some embodiments, the present invention provides novel single-core metallic nanoparticles with hydrodynamic diameters of about 10-100 nm, comprising about 5-25 nm diameter mono- or bi- or tri-metallic cores coated with graft copolymers where the graft copolymers are bound to the metallic core during the sol formation in an aqueous phase.

In some embodiments, the present invention provides nanoparticles that do not lose their water solubility after lyophilization. Thus, the nanoparticles can be particularly useful as matrices for further linking of other molecules, such as adaptors for conjugating macromolecules, linking of dyes and other small molecules. In some embodiments, at least about 80%, about 85%, about 90%, about 95%, or about 98% of the nanoparticles remain soluble after lyophilization.

The terms "imaging moiety" and "therapeutic moiety" are respectively used synonymously with the terms imaging or therapeutic agent. These moieties can be attached to the copolymer via a covalent or non-covalent bond. It will be understood by those having ordinary skill in the art that various imaging and therapeutic moieties can be selected for attachment to functional groups. Further, it will be understood that a linker can be placed between the copolymer shell and the imaging agents and therapeutic agents. The linker can be cleavable or non-cleavable. For example, in certain instances, therapeutic agents can be cleavable. In certain instances, imaging agents can be non-cleavable. The imaging or therapeutic moiety also includes diagnostic agents and targeting agents.

In some embodiments the nanoparticles are attached via a non-ionic bond, to an imaging agent or a therapeutic agent. Therapeutic agents include any therapeutic compounds that are capable of preventing or treating a disease in a patient. Numerous therapeutic agents are known in the art. In some embodiments, therapeutic agents can be, but are not limited to, steroids, analgesics, local anesthetics, antibiotic agents, chemotherapeutic agents, immunosuppressive agents, anti-inflammatory agents, antiproliferative agents, antimitotic agents, angiogenic agents, antipsychotic agents, central nervous system (CNS) agents; anticoagulants, fibrinolytic agents, growth factors, antibodies, ocular drugs, and metabolites, analogs, derivatives, fragments, and purified, isolated, recombinant and chemically synthesized versions of these species, and combinations thereof.

Representative useful therapeutic agents include, but are not limited to, anticancer drugs, aspartic acid analogues meso-tetraphenylporphine, dexamethasone, benzodiazepines, allopurinol, acetohexamide, benzthiazide, camptothecin, cisplatin, chlorpromazine, chlordiazepoxide, doxorubicin, haloperidol, indomethacine, lorazepam, methotrexate, methoxsalen, metformin, methylprednisone, nifedipine, oxazepam, oxyphenbutazone, paclitaxel, prednisone, prednisolone, pyrimethamine, phenindione, sulfisoxazole, sulfadiazine, tamoxifen, temazepam, sulfamerazine, ellipticin, porphine derivatives for photo-dynamic therapy, vinblastine, and/or trioxsalen, short interfering ribonucleic acid (siRNA) molecules, antibiotics such as penicillin and penicillin derivatives, fluoroquinolones, and cephalosporins. In addition to the active therapeutic agents, targeting agents can also be attached to the nanoparticles. Nonlimiting examples include an amino acid sequence including the RGD peptide, an NGR peptide, folate, Transferrin, GM-CSF, Galactosamine, peptide linkers including growth factor receptors (e.g., IGF-1R, MET, EGFR), antibodies and antibody fragments including anti-VEGFR, anti-EGFR, Anti-ERBB2, Anti-tenascin, Anti-CEA, Anti-MUC1, Anti-TAG72, mutagenic bacterial strains, fatty acids and compounds known to specifically binds to a particular biological target. Representative useful imaging agents include, for example, imaging agents useful for medical diagnostics and/or monitoring for one or more of x-ray imaging, fluoroscopy, angiography, mammography, computer aided tomography (CAT), positron emission tomography (PET), single photon emission computerized tomography (SPECT), magnetic resonance imaging (MRI), and ultrasound imaging.

Examples of some imaging and targeting agents include IR dyes, acetylthioacetyl triglycine (MAG3), DTPA, DO3A, DOTA, $^{99m}$Tc, $^{68}$Ga, $^{18}$F, $^{111}$In, and riboflavin 5' monophosphate (RbMP).

The nanoparticles as described herein may also be used in small stable ionic complexes with short negatively charged oligonucleotides and oligonucleotide (deoxyribo- or ribo-) duplexes for enhancing cell uptake for the purpose of, for example, gene silencing and gene delivery.

In some embodiments, MPEG-gPLL is used in GNP synthesis. Unlike GNPs stabilized with PEG-thiols, the synthesis of GNPs stabilized with MPEG-gPLL can be performed via a single step in an aqueous solution. There is no need to form the GNPs and then separately add the stabilizing component using a solution or suspension that then must be removed. Further, the MPEG-gPLL copolymer can contain N-ϵ-acylated PLL, which acts as both capping and reducing component. In many embodiments, the use of MPEG-gPLL can provide stabilization and endcapping, thereby obviating the need for subsequent modifications. In many embodiments, the GNPs according to present teachings carry residual amino groups that promote their association with cells and can be linked to other molecules.

A conjugate of an average-length MPEG methyl carboxylic acid and a 30 kD poly-1-lysine can be used to make the nanoparticles according to some embodiments of the present invention. The use of this copolymer results in highly stable GNPs, even in the presence of a low concentration of trisodium citrate or with no trisodium citrate. MPEG-gPLL is non-immunogenic, non-toxic and is capable of drastically decreasing immunogenicity of the molecules linked to amino groups of MPEG-gPLL. The copolymer and related copolymers are described in Bogdanov et al., Radiology 187:701-706 and Bogdanov et al., Bioconjug Chem 7:144-149, both of which are hereby incorporated by reference in their entirety.

A combination of MPEG-gPLL with citrate or MPEG-gPLL alone can serve as a superior reducing/capping reagent for synthesizing nanoparticles according to present teachings, and can provide a platform for conjugating the nanoparticles to a variety of ligands and drugs due to the presence of free amino groups on the surface of MPEG-gPLL stabilized nanoparticles. Such nanoparticles may also be synthesized in accordance with the present teachings in a convenient "PCR format" that allows handling and manipulating an array of samples with various reactants and desirable temperatures and enable rapid reaction quenching at desired times. Moreover, the synthesis can be scalable and purification of the nanoparticles can be accomplished by using ultrafiltration. The synthesized nanoparticles can exhibit excellent stability in solution upon storage in the presence of phosphate anion and serum.

The graft copolymers may comprise a plurality of poly (ethylene glycol) chains or a derivative thereof, which is grafted to a side chain (R2) of a polyamino acid bearing amino groups. In some embodiments, approximately 10-50% of the amino groups are free and available for further chemical modification. Thus, the nanoparticles as described herein may have both derivatizable (reactive) amino groups and protective groups, where amino protective groups can participate in metallic core formation, and the reactive amino groups on the surface, which can stabilize small, uniform metallic cores, can allow bioconjugation, labeling, lyophilization and subsequent reconstitution in water solutions. In some embodiments, the copolymer N-ϵ-amino group is acylated. In some embodiments, approximately 5-25% of the copolymer N-ϵ-amino groups are acylated. In other embodiments, approximately 10-20% of the copolymer N-ϵ-amino groups are acylated. In other embodiments, approximately 10-15% of the copolymer N-ϵ-amino groups are acylated.

In some embodiments, the PEG portion of the copolymer contains in the range of about 10 to about 500 repeat units, for example, in the range of about 20 to about 220 repeat units. The PEG may be a derivative of PEG or a derivative of MPEG. In some embodiments, the PEG derivative is an ester derivative. In some embodiments, the PEG derivative contains a linker group that comprises a thioether, ether, or an ester and a terminal portion that is an acid group, a succinate, an aryl, or a halo-substituted aryl. In some embodiments, the PEG derivative is an N-hydroxysuccinimide ester, an imidazolide, a pentafluorophenyl ester, an ethylthioacetate of PEG or more preferably MPEG, or said derivative is O-Methyl (PEG))-O'-succinate. In some embodiments, the copolymer is defined by the structure:

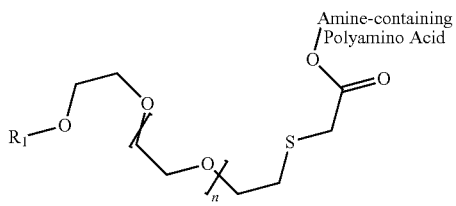

wherein $R_1$ is hydrogen or a lower alkyl and n is 20-220.

In some embodiments, the polyamino acid portion of the copolymer is a poly-L-lysine, a poly-D-lysine, or a mixture thereof. In some embodiments, the PLL component of the copolymer has a molecular weight in the range of about 20 to about 40 kDa and in some embodiments, the molecular weight of the PLL component is about 30 kDa.

In some embodiments, the MPEG-gPLL can stabilize the GNP where the degree of modification of PLL with MPEG is about 5-20%, about 5-15%, about 5-10% or about 10-15%. Higher degree of modification can result in slower nucleation of GNPs, which may not result in as stable GNPs.

In some embodiments, the MPEG-gPLL is formed without a cleavable ester bond. Nanoparticles made using this copolymer can be highly stable. The use of a "cleavable" ester bond, such as the linked MPEG succinate bond, can require careful buffering of the metal solution, for example, such as with citrate before combining the metal with the copolymer (e.g. MPEG-succinyl-gPLL) and forming the nanoparticle. Formation of nanoparticles containing a cleavable ester bond can require the use of relatively low temperatures and long incubations (days). Though the use of a sulfur-containing MPEG analog is not generally required for obtaining stable and homogenous nanoparticles, in some embodiments the use of a plurality of sulfur-gold bonds can result in a highly stable preparation as exemplified below and characterized as 'GNP3' nanoparticles. Though not wishing to be bound by theory, in some embodiments, this is believed to be due to an additional sulfur-gold bond formation in MPEG ethylthioacetate chains, which is similar to previously described bonds between colloidal gold and methionine residues [35].

In some embodiments, the nanoparticles have a hydrodynamic diameter in the range of about 5-500 nm, about 10-100 nm, or about 15-70 nm, comprising a metallic core coated with a graft copolymer. The nanoparticle comprises a metallic core and a polymeric shell. The shell can cover at least about 50, about 60, about 70, about 75, about 80 percent or more of the metallic core and can be attached, at least in part, to the core via metal-amine bonds. In some embodiments at least about 50% of the copolymers coating the metallic core are non-ionically bound to the metallic core. In some embodiments, at least about 60%, about 70%, or about 80% of the copolymers coating the metallic core are non-ionically bound to the metallic core via amine moieties.

In some embodiments, the synthesis of the nanoparticles as described herein can be made by using the copolymers as described herein with the colloidal synthesis as described in Alexandridis, U.S. Pat. No. 7,718,094, which is incorporated herein by reference.

In one exemplary embodiment, nanoparticles are synthesized by mixing water solution of gold (III) chloride optionally mixed with tetrachloroplatinate(II) or silver (I) chloride in the ratio of no less than 2Au:1Me by weight (where Me is Ag and/or Pt) with a water solution of a graft copolymer at a temperature in a range of about 90-99° C. The formation of nanoparticles with characteristic 525-650 nm plasmon peak that depends on the ratio of graft copolymer/Au is used as the endpoint of the reaction. After quenching on ice the nanoparticles are purified using one-step procedure including centrifugation through a cushion of 5-8% non-ionic contrast agent iodixanol at 50,000×g and optional desalting using conventional ultrafiltration, dialysis or centrifugal diafiltration. The latter steps are compatible with GLP and cGMP requirements In many embodiments of the invention, thiolation is not required for the nucleation and aggregation of the nanoparticles. Thus, the nanoparticles can be made without adding a thiol or derivatizing a polymer or copolymer to contain thiol groups. In another embodiments, a small amount of thiol-containing compound can be included in the reaction mixture. When using such thiol-containing compound, it is desirable to use a concentration of the compound that would not substantially interfere with the formation of amine-metal bonds. For example, the molar concentration of the thiol is less than about 25%, less than about 10%, or less than about 5% of the molar concentration of the protective amine groups.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto.

EXAMPLES

Aspects of the applicant's teachings may be further understood in light of the following examples, which should not be construed as limiting the scope of the present teachings in any way.

Example 1

Polymer Synthesis

Poly(ethylene glycol) monomethyl ether, MPEG5000 (Mn=5000) was obtained from Sigma-Aldrich. Dichloromethane ($CH_2Cl_2$) and dioxane were purified by distillation over calcium hydride. Derivatives of MPEG as shown in Scheme 1 were then prepared.

Scheme 1

Methoxy poly(ethylene glycol) derivatives.

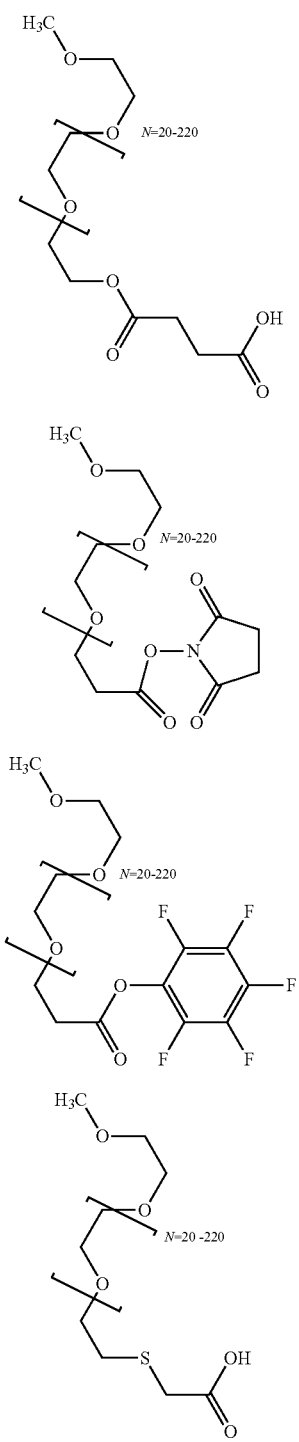

Synthesis of MPEG Derivatives (Scheme 1).

O-Methyl Poly(ethylene glycol)-O'-succinate (1) was prepared by refluxing 1 mmol MPEG5000 with 5-molar excess of succinic anhydride in the presence of 1.1 mmol 4-dimethylaminopyridine (DMAP) in dry dioxane for 5 h at 80° C. under argon. The reaction mixture was evaporated in vacuum, dissolved in chloroform, filtered through a layer of Celite and purified by repeated precipitations using a mixture of diethyl ether:ethyl acetate (4:1 v/v) on ice. The final precipitate was dissolved in water, the pH was adjusted to 3, passed through 10 g of ethanol/water washed AG50 W-X8 resin, and lyophilized. Yield-65% compared to theoretical.

N-hydroxysuccinimide ester of methoxy MPEG5000 methyl carboxylic acid (2). Synthesis of MPEG5000 chloroformate was performed as in [11]. Briefly, a solution of 1 mmol of MPEG5000 in toluene was refluxed in a Dean-Stark apparatus and dried. Dry MPEG5000 was dissolved in anhydrous dicholoromethane and treated with 1 mL of phosgene solution in toluene (1.9 mmol) and the mixture was stirred overnight. Toluene was evaporated and the chloroformate derivative of MPEG was re-dissolved in 10 mL of anhydrous methylene chloride. The obtained chloroformate was reacted with 10% molar excess of N-hydroxysuccinimide in anhydrous $CH_2Cl_2$ to yield the corresponding N-hydroxusuccinimide ester (2) that was purified by repeated precipitation with diethyl ether. Alternatively, a modified method of Miron and Wilcheck [12] was used to obtain N-hydroxusuccinimide ester and pentafluorophenyl activated ester (3) of MPEG carboxylate. Briefly, 1 mmol of dry MPEG was combined with 10 mmol of N,N'-disuccinimidyl carbonate or bis(pentafluorophenyl) carbonate in 30 ml of dry dioxane followed by 10 mmol of 4-dimethylaminopyridine in dioxane. The reaction mixture was kept at room temperature overnight under argon and the product was purified by 3 re-precipitations as described above. Yield-70% compared to theoretical.

MPEG ethylthioacetate (4) was synthesized using MPEG tosylate as a starting compound. Tosylation of MPEG was accomplished by dissolving a toluene-dried 1 mmol MPEG in 30 ml dry $CH_2Cl_2$ containing 2 mmol dry triethylamine and adding 5-molar excess of p-toluenesulfonyl chloride in 15 ml dry dioxane over 1 h at 0° C. The reaction mixture was stirred for 48 h under argon and filtered through a layer of Celite. The solvents were removed under vacuum and MPEG tosylate was re-precipitated 4 times from $CH_2Cl_2$ using ethyl ether/ethyl acetate (4:1 v/v), re-dissolved in $CH_2Cl_2$ and washed once with 0.1 M HCl followed by drying over $Na_2SO_4$. The organic phase was evaporated and the obtained product (approximately 0.7 mmol in 15 ml $CH_2Cl_2$ was added drop-wise to a 2-fold molar excess of mercaptoacetic acid in 30 ml of dioxane containing 2 mmol 4-dimethylaminopyridine under argon and reacted for 16 h). The reaction mixture was evaporated to dryness, dissolved in dichloromethane and washed with 0.1M HCl supplemented with NaCl (final concentration—3M), extracted once using $CH_2Cl_2$. The organic phase was dried under vacuum, and filtered through 0.2 μm glass fiber disks, re-dissolved in water and freeze-dried. The yield of 4 was 50% from theory.

Example 2

Synthesis of MPEG-gPLL Copolymer (Scheme 2)

Synthesis of graft copolymer of MPEG5000 and PLL was accomplished using two approaches: 1) by using water soluble carbodiimide activation of 1 or 4 in the presence of N-hydroxysulfosuccinimide as originally described in [13, 14]. 2) by using activated MPEG ester-mediated direct acylation of poly-1-lysine.

Scheme 2

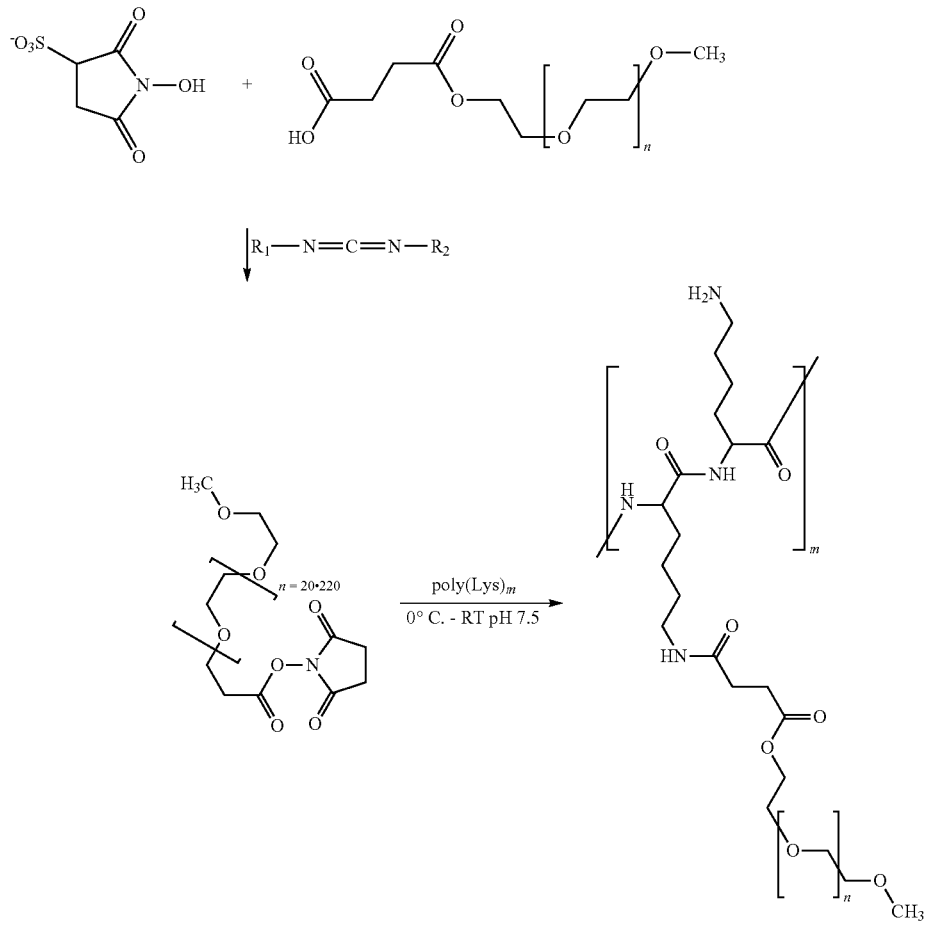

Method 1.

100 mg of poly-1-lysine hydrobromide (PLL m.w 34.4 kD, d.p. 164, Sigma-Aldrich) was dissolved in ice-cold 20 ml of 0.1 M NaHCO$_3$ buffer, pH 8.7 (approximately 25 mM amino groups). One g of 1 or 4 and 40 mg (0.2 mmol) of N-hydroxysulfosuccinimide were dissolved in 2 ml of water and mixed with a solution of 100 mg of 1-(3-dimethyl aminopropyl)-3-ethyl carbodiimide, hydrochloride (EDC, 0.52 mmol) in 0.5 ml water and incubated for 5 min with mixing. The activated solutions of 1 or 4 were added to the solution of PLL and the reaction mixture was incubated overnight at RT under argon. The obtained product was purified by ultrafiltration using UFP-300 cartridges (GE Healthcare) or partially purified using Amicon Ultracel YM-50 (EMD-Millipore) and lyophilized. The degree of N-ε-amino group acylation was determined using trinitrobenzene sulfonic acid (TNBS). The residual content of MPEG5000 in the product did not exceed 10% by HPLC (Superdex200, GE Healthcare).

Method 2.

MPEG-gPLL was prepared as above except that activated MPEG carboxylates (i.e. 1 g of either NHS ester 2 or pentafluorophenyl ester 3 of MPEG5000) were added to PLL solution as dry powders in 100 mg portions on ice followed by mixing. The purification was performed as above.

Modification of MPEG-gPLL amino groups was performed by using a 10-fold molar excess of dry succinic anhydride over TNBS-reactive N-ε-amino groups in MPEG-gPLL (20 mg/ml in 0.1 M NaHCO$_3$, pH 7.7) on ice followed by 2 h incubation and dialysis. Alternatively, acetylated MPEG-gPLL was synthesized by adding a 10-fold molar excess of acetic acid N-hydroxysuccinimide ester (Sigma-Aldrich) to PLL (20 mg/ml in 0.1 M NaHCO$_3$, pH 7.7) followed by a 2 h incubation at RT and dialysis. The completeness of N-ε-amino group modification was determined by TNBS test.

MPEG-gPLL Synthesis.

The linking of MPEG chains to PLL backbone resulted in graft copolymers with excellent solubility in water in the pH range of 3-9, i.e. enabling synthesis of GNPs both in the presence and the absence of trisodium citrate. Size exclusion HPLC on Superdex200 revealed a single major peak corresponding to hydrodynamic diameter of a 300-400K protein. The minor impurities of free MPEG did not interfere with GNP synthesis. Using TNBS we determined that MPEG-gPLL contained approximately 10-15% of PLL N-ε-amino groups. Higher numbers of conjugated MPEG chains (i.e. 20-25% conjugated N-ε-amino groups of PLL commonly used in our previous work) resulted in MPEG-gPLL preparations that did not support the formation of spherical GNPs and were not used in further work [18, 19].

Example 3

Synthesis of Gold Nanoparticles

PCR plate format synthesis. MPEG-gPLL (120 mg/ml H$_2$O, approximately 0.3 mM) was serially diluted 2× in a 96-well titer plate. HAuCl$_4$ solution in H$_2$O was diluted to 160, 140, 110, 80 μM in water. 0.2 ml of these solutions were placed in polypropylene PCR plate (USA Scientific), sealed and heated to 95° C. using a PCR Peltier thermocycler (PTC-200, MJ Research, Watertown Mass.). After 5 min, 20 μl of serially diluted solutions of MPEG-gPLL were added to the wells of the PCR plate using a multipipette and the plate was re-sealed and heated at 95° C. for additional 30 min. The plate was quickly cooled to 0° C. in the thermocycler unit and the contents of the wells were transferred to 96-well plate to measure the absorbance spectra in the range of 400-700 nm using Spectramax M5 plate reader (Molecular devices) to establish the position of a plasmon peak.

The General GNP Synthesis Scale-Up Procedure.

A 0.14 mM solution of HAuCl$_4$ was prepared in 100 ml of degassed dioinized H$_2$O saturated with nitrogen, using an internal probe to monitor temperature. The solution was quickly heated to 95° C. for 5 min using a water jacket and a solution of 90 mg MPEG-gPLL (native, succynilated or acetylated) in 4 ml H$_2$O was injected with stirring. In partially purified MPEG-gPLL the graft copolymer content was adjusted according to the results of HPLC purity analysis using 240 nm absorbance data corresponding to the absorbance of MPEG. The final concentration of N-ε-amino groups in the GNP reaction mixture was approximately 0.4 mM. In some experiments trisodium citrate, pH 8.0 was added to the GNP reaction mixture together with MPEG-gPLL to achieve the final concentration of 0.1-0.4 mM of trisodium citrate. The heating continued for 30 min and the GNP reaction mixture was immersed in ice-water mixture followed by filtering through 0.22 μm membrane using sterile Steriflip-GV PVDF membrane units (Millipore) for storage prior to the purification.

The separation from free MPEG-gPLL was accomplished by loading 16 ml of GNP on top of an 8% solution of Opti-Prep (60% Iodixanol solution in saline, Sigma-Aldrich, initial density 1.32 g/ml) in Oak Ridge PPCO 50 ml centrifuge tubes (Nalgene) and centrifuged in JA25.5 rotor (Beckman) at 22,000×rpm for 60 min. The supernatant was removed and the dense dark-colored bottom 1 ml fraction was collected. 6 ml of pooled GNP fractions were loaded on 30 ml of 6% solution of Opti-Prep in 30 mM Hepes, pH 8.0 and centrifuged as described above for 45 min. The bottom 1 ml fraction was collected, vortexed and washed with water using Amicon Ultra 4 YM-100 centrifuge membrane concentrators (EMD-Millipore) as suggested by the manufacturer. Alternatively, filtered GNP solutions were loaded in Flex-Stand system equipped with a UFP-500-E-5A ultrafiltration cartridge with a cut-off of 500 kD (A/G Technologies-GE Healthcare) and washed using 30 L of 150 mM NaCl. The purity of nanoparticles was determined using Superdex200 size-exclusion HPLC columns eluted with 0.1M ammonium acetate buffer. In some cases the particles were pre-labeled using high extinction coefficient IR Dye 6804 NHS ester (Li-Cor Inc, Lincoln Nebr.) for detecting PGC impurities in GNP preparations as described below. After the washings the particles were pooled and lyophilized. The lyophilized particles were reconstituted in PBS at 10 mg/ml for further experiments.

Nanoparticle Synthesis.

Figure 1B:
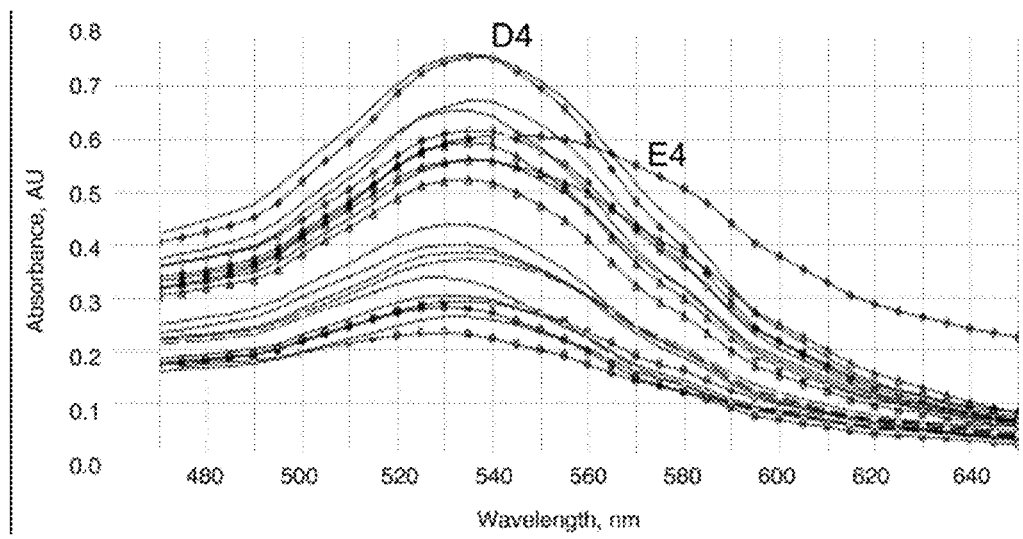
Figures 6A, 6B:
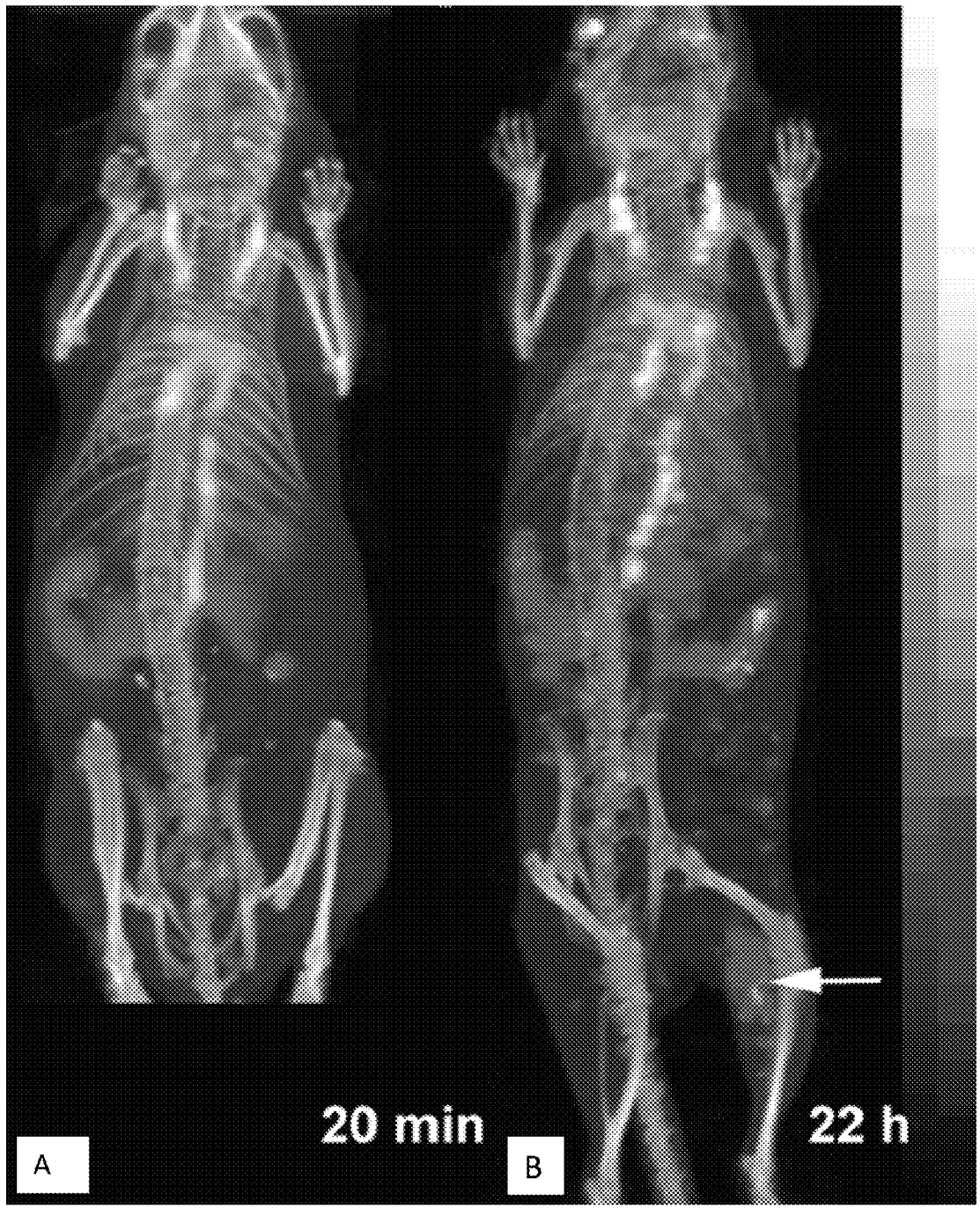
FIGS. 6A-6B. SPECT/CT imaging of 99 mTc labeled MAG3-GNP3 according to an embodiment of the present teachings, after injection into DBA2 mice harboring experimental LPS induced inflammatory lesions in the right extremity.

The effect MPEG-gPLL graft copolymer and the concentration of hydrogen tetrachloroaurate using an optimization format in PCR plates was investigated. The investigation varied the concentration of HAuCl$_4$ in the range 80 and 160 μM and the concentration of MPEG-gPLL in the range of 2.4-0.3 mg/ml to determine conditions that would result in the formation of nanoparticle preparations with acceptable LALLS intensity and high plasmon intensity peaks (FIGS. 1A-1B and Table 1).

TABLE 1

Characterization of GNP (Particle size matrix, see FIGS. 1A and 1B) showing scattering intensity hydrodynamic diameter (nm), Plasmon intensity and Plasmon peak maxima.

| | Z-average hydrodynamic diameter (nm); Absorbance at $\lambda_{max}$; $\lambda_{max}$ peak position (nm) | | | |
|---|---|---|---|---|
| | 1 | 2 | 3 | 4 |
| A | 159 nm; 0.232 530 nm | 122 nm; 0.336 530 nm | 108 nm; 0.523 535 nm | 116 nm; 0.616 535 nm |
| B | 149 nm; 0.261 530 nm | 109 nm; 0.372 535 nm | 76 nm; 0.560 535 nm | 43 nm; 0.672 535 nm |
| C | 34 nm; 0.292 530 nm | 52 nm; 0.385 535 nm | 49 nm; 0.593 535 nm | 43 nm; 0.756 535 nm |
| D | 33 nm; 0.303 530 nm | 35 nm; 0.437 535 nm | 36 nm; 0.653 535 nm | 41 nm; 0.760; 535 nm |
| E | 40 nm; 0.281 530 nm | 37 nm; 0.398 535 nm | 39 nm; 0.561 535 nm | 41 nm; 0.608 540 nm |

During the optimization the investigation considered the rate of capping graft-copolymer addition and minimized the cooling of the plate during the addition by using a Peltier device with rapid heat exchange. The results of titrations (FIGS. 1A and 1B) showed that the acceptable concentration range for HAuCl$_4$ concentrations for this example was 140-160 μM while the concentration of MPEG-gPLL should be above 0.15 mg/ml under the conditions provided in this example. Both low molecular weight capping agent (i.e. trisodium citrate) free and citrate-containing solutions of MPEG-gPLL resulted in formation of GNP. However, the lack of citrate resulted in more microaggregates (as demonstrated by TEM) and citrate-free approach was not used in scale-up synthesis. Trisodium citrate was also replaced by bis(carboxymethyl)lysine with the formation of GNPs at the temperatures of 90-99° C. The use of succynilated or acetylated MPEG-gPLL resulted in formation of predominantly 2:1 nanorods (Table 2) with a characteristic Plasmon peak widening and peak shift to 575 nm. The formation of nanorods was facilitated by the addition of 30-35 mM trisodium citrate (final concentration). The use of MPEG-gPLL in which MPEG was linked to PLL via the ester bond, e.g. obtained by using of Omethylpoly(ethylene glycol)-O'-succinate (1), during the synthesis did not facilitate the formation of GNPs if no trisodium citrate was added. The reduction and capping with the formation of GNPs in the presence of 1 was successful only at room temperature and required incubating the reaction mixture at room temperature for 2 days. Therefore, the investigation used MPEG-gPLL synthesized by using 2, 3 or 4, i.e., non-cleavable MPEG chains for future scale-up synthesis. The scale up synthesis performed at 0.14 mM HAuCl$_4$, i.e. at the intermediate concentration of HAuCl$_4$ and intermediate acceptable MPEG-gPLL concentration of 0.9 mg/ml, resulted in nanoparticles with 9.3±2.6 solid cores and average hydrodynamic diameters of 69.6 nm ("GNP3", Table 2). Compared to highly negatively charged citrate GNP, GNP3 were mainly weakly positively charged and carried amino groups that were reactive with TNBS (Table 2). The peaks corresponding to small (6-7 nm) and strongly positively charged molecules (i.e. MPEG-gPLL) were present in GNP reaction mixtures (FIGS. 2A-2D). These contaminations were undetectable in GNPs preparations that were subjected to purification using gradient centrifugation and/or ultrafiltration (FIGS. 2C and 2D). MPEG-gPLL capped GNP3 did not aggregate in the presence of phosphate anion (PBS, Table 2), nor did they adsorb on the surface of polysaccharide microporous (i.e. BioGel P-30) and macroporous (Superdex) gel-filtration beads. This allowed the use of size-exclusion chromatography for purity analysis and for purification GNP3 from low molecular weight compounds after the modification. If present, the traces of MPEG-gPLL impurity could be revealed by using size-exclusion chromatography after a linking of high extinction coefficient near-infrared fluorescence dye NHS-ester to the components of the reaction mixture followed by separating the IR-Dye labeled components (FIGS. 3A-3D). The presence of reactive amino groups on GNP3 surface also resulted in labeling as suggested by the presence of a shoulder on 680 nm trace (FIG. 3A). Transmission electron microscopy of GNP3 after size-exclusion chromatography revealed solid core spherical nanoparticles (FIGS. 4A and 4B) surrounded by polymeric corona that resulted in characteristic halo shading that was clearly visible on scanning electron microcopy images (FIG. 4C). Linking of riboflavin monophosphate that was used as a model small molecular mass ligand showed that phosphate groups could be easily linked to GNPs with the formation of phosphamides. The linking of riboflavin resulted in a shift of GNP3 zeta potential from weakly positive to negative (i.e. from average +3.7 to −12.9, Table 2).

diameter by laser light scattering, numerical average) was recorded. 0.5 ml to 2 ml of particles were diluted to 10 ml in DDW and 10-20 µl of gold (III) chloride (120 mg/ml) was added followed by 0.3 ml 1% trisodium citrate or 0.5 ml 0.1 M ammonium acetate (pH7.0) with mixing. The formation of stabilized GNPs was initiated by adding 20-40 mg of MPEG-gPLL per 10 ml of solution containing the mixture of silver-iron oxide nanoparticles and gold(III) chloride. The formation of iron oxide-silver-gold nanoparticles was observed with or without heating of the mixture to 95° C. The particles were purified by sterile filtration through a 0.2 µm membrane, concentrated using Amicon Ultra 4 YM-100 centrifuge membrane concentrators (EMD-Millipore) and purified by centrifugation through a 15% solution of Opti-Prep (60% Iodixanol solution in saline, Sigma-Aldrich, initial density 1.32 g/ml) at 35,000 rpm in SW41Ti rotor for 30 min. The obtained nanoparticles had a hydrodynamic diameter of 30.9±9.6 nm and high transverse molar relaxivity values shown in Tables 3 and 4:

TABLE 3

Longitudinal Relaxivity

| | Longitudinal relaxivity r1 ($mM^{-1}s^{-1}$) | |
|---|---|---|
| | 0.47 T | 3 T |
| Iron oxide nanoparticles (IONP) | 22.66 | 5.30 |
| IONP/silver | 28.2 ± 5.5 | 42.72 |
| IONP/silver/gold | 44.2 ± 1.8 | 60.46 |
| MPEG-gPLL-stabilized IONP/silver/gold | 33.44 | 24.91 |

TABLE 2

Major properties of GNP preparations synthesized in the absence and the presence of MPEG-gPLL

| Sample | Description | Size (nm) | Core size, EM (nm) | Aggregation in PBS, pH 7.4 | Retention* | Zeta potential (mV) | Amino groups |
|---|---|---|---|---|---|---|---|
| GNP0 | Trisodium citrate nanoparticles | 14.63 ± 11 | 20 nm | yes | 0.68 ± 0.14 nm (retained on the column) | −21 ± 10 | Not detectable |
| GNP1 (nanorods 2:1) | Reduced with citrate in the presence of succinylated MPEG-gPLL | 64.9 ± 20.7 | NA | no | NA | −4.37 ± 7.8 | Not detectable |
| GNP3 | MPEG-gPLL reduced | 69.6 ± 29.3 | 9.28 ± 2.57 | no | 33.5 ± 9.7 | 3.7 ± 9.8 | 1.10-6 mol/AU |
| GNP3-Rbf 10.5 | GNP3 conj to Rbf | | NA | no | 33.4 ± 10.7 | −12.9 ± 7.0 | Not detectable |

*Retention is on Bio-Spin P6, size of flow through

Synthesis of Nanoparticles with Mixed Cores.

Dextran-stabilized iron oxide (2-5 mg of iron/ml) was treated with 50 mM solution of $Ag(NH_3)_2NO_3$ (a solution of silver (I) nitrate in ammonia) for 10 min at 95° C. A PD-10 spin-column was filled with Sephadex G-25m, which was pre-equilibrated with double-deionized water (DDW). The column was spun at 1000×g for 5 min. The silver-treated iron oxide nanoparticles were pipetted on the top of Sephadex in the column. The columns were spun at 1000×g for 5 min. The flow-through was collected and the increase of nanoparticle diameter from 20.5±4.6 nm to 34±9.5 nm (hydrodynamic

TABLE 4

Transverse Relaxivity

| | Transverse relaxivity r2 ($mM^{-1}s^{-1}$) | |
|---|---|---|
| | 0.47 T | 3 T |
| Iron oxide nanoparticles (IONP) | 44.68 | 54.53 |
| IONP/silver | 55.2 ± 4.9 | 659.94 |
| IONP/silver/gold | 106.8 ± 13.3 | 723.64 |

TABLE 4-continued

Transverse Relaxivity

| | Transverse relaxivity r2 (mM$^{-1}$s$^{-1}$) | |
|---|---|---|
| | 0.47 T | 3 T |
| MPEG-gPLL-stabilized IONP/silver/gold | 71.51 | 652.52 |

Example 4

Linking to Gold Nanoparticles

Linking of MAG3-NHS Ester to GNP and 99 mTc Labeling.

The modification of GNPs with acetylthioacetyl triglycine (MAG3) was performed as described in [15]. Non-bound MAG3 was removed using Bio-Spin30 centrifugation minicolumns (Bio-Rad) as described by the manufacturer or on Sephadex G-25m (10×1 cm column, Sigma-Aldrich) using gravity size-exclusion chromatography. The labeling procedure that involved labeling with simultaneous de-protection of thiols is described in detail in [16]. The radiolabeling purity was determined using ITLC-G and HPLC.

Conjugation of riboflavin-5'-monophosphate (RbMP) was accomplished using phosphamide bond formation as suggested in [17]. Briefly, 0.07 mmol of RbMP in 0.5 ml in 0.2 M 1-methylimidazole was mixed with 0.14 mmol of EDC in 0.5 ml water on ice for 10 min and added to 0.2 ml of GNP (1 mg solid) dissolved in 0.2 M NaHCO$_3$. The GNPs were purified by dialysis and the absorbance ratio at 445 and 530 nm (i.e. plasmon peak maximum) were determined for the control and conjugated GNP, respectively. The extinction coefficient of RbMP at 445 nm was 13,000 [mol. cm]$^{-1}$.

Example 5

Cell Culture Experiments

Cell culture experiments were performed in human umbilical vein endothelial cells (HUVEC), HeLa and PANC-1 cells. HUVEC cells were grown in 5% FBS, complete endothelial cell growth medium (EGM, Lonza, Hopkinton, Mass.) until confluent. PANC-1 cells were grown in 10% FCS, DMEM and HeLa cells were grown in 10% EMEM. Cells were incubated for 24 hrs with various concentrations of GNP3 for 24 hrs prior to determining the toxicity. Cytotoxicity of GNP in the cell culture was measured using a 96-well format and a standard WST reagent assay and measuring the formation of red formazan compound at 500 nm using a plate reader. The WST signal will be normalized using background (reference) measurements at 650 nm.

To test the effects of non-conjugated, weakly positively charged GNP3 on normal human cells and human cancer cells the nanoparticles were membrane sterilized and incubated in complete medium (in the presence of 10% serum) with the cells in 96-well plates at various concentrations. The TEM images showed the uptake of nanoparticles in endosomes with most of the nanoparticles showing no adsorption on the luminal surface of endosomes (FIG. 5A) while in later organelles that showed fusion with endosomes nanoparticles appeared more aggregated and associated with the membranes (FIG. 5B). The cancer cells that showed the high level of uptake (PANC-1) GNP3 resulted in a dose-dependent toxic effects (approximately 50% cell survival at 500 µg Au/ml) whereas in normal HUVEC only a 8±2% decrease of cell viability was detected at the same dose (FIG. 5C).

Example 6

Animal Experiments

The animal protocol involving 99 mTc-labeled GNP injections IV were approved by the University of Massachusetts Medical School IACUC committee. The mice (DBA/2Ncr, n=2) were implanted with 0.1 mL of Matrigel (Beckton-Dickinson) containing 5 µg LPS from *E. coli* (Sigma-Aldrich) in the right femoral muscle 16 h before the experiment. The left leg was implanted with the same volume of Matrigel containing no LPS. The animals were injected IV with 0.2 mL of GNP-MAG3 labeled with 99 mTc (20 µg solid from reconstituted lyophilized GNP), anesthetized and imaged 10 min, 4 h and 26 h after the injection using NanoSPECT/CT (Bioscan). Ectopic tumor model was obtained by implanting 1.106 PANC-1 cells in the right flank of female nu/nu mice. Tumors reached the size of 0.5 cm in diameter in 3 weeks after which animals were injected with GNP-MAG3 as described above. The animals were sacrificed after the last imaging session (or at 26 h post I.V. injection) and biodistribution in major organs was determined by using gamma-counting (Packard).

The GNP3 nanoparticle preparation was tested in two animal models: experimental soft tissue inflammation (myositis) and cancer model (an ectopic pancreatic cancer xenograft model). GNP3 were efficiently labeled with 99 mTc (labeling efficiency 75-90%) and purified using BioSpin P30 columns. The experiments in two model systems showed that GNP3 have long circulation times. The nanoparticles showed a linear pattern of elimination from the blood stream suggesting zero-order kinetics with T½=47.5±17.5 h. GNP3 showed enhanced accumulation in the areas of enhanced vascular permeability (tumor, experimental inflammatory lesion). The target to background (i.e. the ratio of normalized radioactivity measured in inflamed extremity vs control non-affected leg, and tumor vs contralateral muscle) ratios ranged between 1.5 to 3.1.

The most remarkable results were observed in cell culture and in vivo experiments. The combination of a lack of aggregation after the uptake combined with high cytotoxicity in pancreatic cancer cells and accumulation in tumors in vivo suggest potential future applications in tumor targeting for delivery of GNP. The targeting is expected to be feasible due to the very long circulation of GNP3 in the bloodstream due to the lack of recognition of GNP3 by reticulo-endothelial system.

Example 7

Additional examples are found in Appendix A, entitled "Soft-matter" meets condensed matter: synthesis and in vivo testing of long-circulating biocompatible stable gold nanoparticles.

The section headings used herein are for organizational purposes only and are not to be construed as limiting the subject matter described in any way. All publications are herein incorporated by reference in their entirety.

While the present invention teachings are described in conjunction with various embodiments, it is not intended that the invention be limited to such embodiments. On the contrary, the present invention encompasses various alternatives, modifications, and equivalents, as will be appreciated by those of skill in the art.

REFERENCES

1. Mackiewicz M R, Hodges H L, Reed S M. (2010) C-reactive protein induced rearrangement of phosphatidylcholine on nanoparticle mimics of lipoprotein particles. J Phys Chem B 114:5556-5562
2. Ge C, Fang Z, Chen J, et al. (2012) A simple colorimetric detection of DNA methylation. Analyst 137:2032-2035
3. Lin Y W, Huang C C, Chang H T. (2011) Gold nanoparticle probes for the detection of mercury, lead and copper ions. Analyst 136:863-871
4. Nusz G J, Curry A C, Marinakos S M, Wax A, Chilkoti A. (2009) Rational selection of gold nanorod geometry for label-free plasmonic biosensors. ACS Nano 3:795-806
5. Zijlstra P, Paulo P M, Orrit M. (2012) Optical detection of single non-absorbing molecules using the surface plasmon resonance of a gold nanorod. Nat Nanotechnol 7:379-382
6. Cherukuri P, Glazer E S, Curley S A. (2010) Targeted hyperthermia using metal nanoparticles. Adv Drug Deliv Rev 62:339-345
7. Butterworth K T, Coulter J A, Jain S, et al. (2010) Evaluation of cytotoxicity and radiation enhancement using 1.9 nm gold particles: Potential application for cancer therapy. Nanotechnology 21:295101
8. Chithrani D B, Jelveh S, Jalali F, et al. (2010) Gold nanoparticles as radiation sensitizers in cancer therapy. Radiat Res 173:719-728
9. Hainfeld J F, Dilmanian F A, Thong Z, et al. (2010) Gold nanoparticles enhance the radiation therapy of a murine squamous cell carcinoma. Phys Med Biol 55:3045-3059
10. Callahan R J, Bogdanov A, Jr., Fischman A J, Brady T J, Weissleder R. (1998) Preclinical evaluation and phase in clinical trial of a 99mtc-labeled synthetic polymer used in blood pool imaging. A JR American Journal of Roentgenology 171:137-143
11. Banerjee P, Weissleder R, Bogdanov A, Jr. (2006) Linear polyethyleneimine grafted to a hyperbranched poly(ethylene glycol)-like core: A copolymer for gene delivery. Bioconjugate Chemistry 17:125-131
12. Miron T, Wilchek M. (1993) A simplified method for the preparation of succinimidyl carbonate polyethylene glycol for coupling to proteins. Bioconjug Chem 4:568-569
13. Bogdanov A A, Weissleder R, Frank H W, et al. (1993) A new macromolecule as a contrast agent for mr-angiography—preparation, properties, and animal studies. Radiology 187:701-706
14. Bogdanov A A, Jr., Martin C, Bogdanova A V, Brady T J, Weissleder R. (1996) An adduct of cis-diamminedichloroplatinum(ii) and poly(ethylene glycol)poly(1-lysine)-succinate: Synthesis and cytotoxic properties. Bioconjug Chem 7:144-149
15. Winnard P, Jr., Chang F, Rusckowski M, Mardirossian G, Hnatowich D J. (1997) Preparation and use of nhs-mag3 for technetium-99m labeling of DNA. Nucl Med Biol 24:425-432
16. Wang Y, Liu X, Hnatowich D J. (2007) An improved synthesis of nhs-mag3 for conjugation and radiolabeling of biomolecules with (99m)tc at room temperature. Nat Protoc 2:972-978
17. Rasmussen S R, Larsen M R, Rasmussen S E. (1991) Covalent immobilization of DNA onto polystyrene microwells: The molecules are only bound at the 5' end. Anal Biochem 198:138-142
18. Bogdanov A, Jr., Wright S C, Marecos E M, et al. (1997) A long-circulating copolymer in "Passive targeting" To solid tumors. Journal of Drug Targeting 4:321-330
19. Bogdanov A J, Mazzanti M, Castillo G, Bolotin E. (2012) Protected graft copolymer (pgc) in imaging and therapy: A platform for the delivery of covalently and noncovalently bound drugs Theranostics 2(6):553-576
20. Brown C L, Whitehouse M W, Tiekink E R, Bushell G R. (2008) Colloidal metallic gold is not bio-inert. Inflammopharmacology 16:133-137
21. Yarom R, Stein H, Peters P D, Slavin S, Hall T A. (1975) Nephrotoxic effect of parenteral and intraarticular gold. Ultrastructure and electron microprobe examination of clinical and experimental material. Arch Pathol 99:36-42
22. Simpson C A, Huffman B J, Gerdon A E, Cliffel D E. (2010) Unexpected toxicity of monolayer protected gold clusters eliminated by peg-thiol place exchange reactions. Chem Res Toxicol
23. Sakai T, Alexandridis P. (2005) Mechanism of gold metal ion reduction, nanoparticle growth and size control in aqueous amphiphilic block copolymer solutions at ambient conditions. J Phys Chem B 109:7766-7777
24. Dumur F, Guerlin G, Dumas E, et al. (2011) Controlled spontaneous generation of gold nanoparticles assisted by dual reducing and capping agents. Gold Bull 44:119-137
25. Ishii T, Otsuka H, Kataoka K, Nagasaki Y. (2004) Preparation of functionally pegylated gold nanoparticles with narrow distribution through autoreduction of auric cation by alpha-biotinyl-peg-block-[poly(2-(n,n-dimethylamino) ethyl methacrylate)]. Langmuir 20:561-564
26. Yoon S M, Myung S J, Kim I W, et al. (2011) Application of near-infrared fluorescence imaging using a polymeric nanoparticle-based probe for the diagnosis and therapeutic monitoring of colon cancer. Dig Dis Sci 56:3005-3013
27. Sun I C, Eun D K, Koo H, et al. (2011) Tumor-targeting gold particles for dual computed tomography/optical cancer imaging. Angew Chem Int Ed Engl 50:9348-9351
28. Zheng M, Davidson F, Huang X. (2003) Ethylene glycol monolayer protected nanoparticles for eliminating nonspecific binding with biological molecules. J Am Chem Soc 125:7790-7791
29. Heo D N, Yang D H, Moon H J, et al. (2012) Gold nanoparticles surfacefunctionalized with paclitaxel drug and biotin receptor as theranostic agents for cancer therapy. Biomaterials 33:856-866
30. Marchand C, Bachand J, Perinet J, et al. (2010) C3, c5, and factor b bind to chitosan without complement activation. J Biomed Mater Res A 93:1429-1441
31. Bertholon I, Vauthier C, Labarre D. (2006) Complement activation by core-shell poly(isobutylcyanoacrylate)-polysaccharide nanoparticles: Influences of surface morphology, length, and type of polysaccharide. Pharm Res 23:1313-1323
32. Benesch J, Tengvall P. (2002) Blood protein adsorption onto chitosan. Biomaterials 23:2561-2568
33. Arima Y, Toda M, Iwata H. (2008) Complement activation on surfaces modified with ethylene glycol units. Biomaterials 29:551-560
34. Sherman M R, Williams L D, Sobczyk M A, Michaels S J, Saifer M G. (2012) Role of the methoxy group in immune responses to mpeg-protein conjugates. Bioconjug Chem 23:485-499
35. Okada Y, Takano T Y, Kobayashi N, et al. (2011) New protein purification system using gold-magnetic beads and a novel peptide tag, "The methionine tag". Bioconjug Chem 22:887-893

I claim:

1. A nanoparticle comprising:
   a metallic core, and
   a copolymer shell of a polyethylene glycol and an amine-containing polyamino acid that at least partially surrounds the metallic core,
   wherein said copolymer shell is non-ionically bound to said metallic core via metal-amine bonds, and
   wherein said nanoparticle is a non-aggregating nanoparticle, and
   wherein said amine-containing polyamino acid is any of poly-L-lysine and poly-D-lysine.

2. The nanoparticle of claim 1, wherein said nanoparticle has a Zeta potential in the range of about −14 to about +10 mV.

3. The nanoparticle of claim 1, wherein said metallic core is about 5-25 nm in diameter and the nanoparticle has a hydrodynamic diameter in the range of about 10-100 nm.

4. The nanoparticle of claim 1, wherein said polyethylene glycol comprises about 90-95% and said amine-containing polyamino acid comprises about 5-10% of said copolymer.

5. The nanoparticle of claim 1, wherein said metallic core comprises gold.

6. The nanoparticle of claim 1, wherein said metallic core comprises gold and one or more of platinum (II) and silver.

7. The nanoparticle of claim 1, wherein said copolymer is acylated at the N-ε-amino.

8. The nanoparticle of claim 7, wherein approximately 10-20% of the copolymer N-ε-amino groups are acylated.

9. The nanoparticle of claim 1, wherein said polyethylene glycol is a methoxy polyethylene glycol (MPEG) or derivative thereof.

10. The nanoparticle of claim 9, wherein said derivative of MPEG is an N-hydroxysuccinimide ester, imidazolide, a pentafluorophenyl ester, or an ethylthioacetate of MPEG or said derivative is O-Methyl(PEG))-O'-succinate.

11. The nanoparticle of claim 1, wherein said copolymer has the structure:

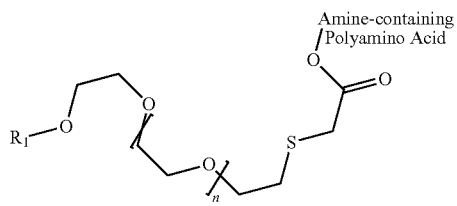

wherein $R_1$ is hydrogen, a lower alkyl, or a protecting group and n is 20-220.

12. The nanoparticle of claim 1, wherein at least about 50% of the copolymers in said shell are non-ionically bound to said metallic core via metal-amine bond.

13. The nanoparticle of claim 1, wherein said copolymer shell covers at least about 50 percent of said metallic core.

14. The nanoparticle of claim 1, wherein said copolymer shell covers at least about 75 percent of said metallic core.

15. The nanoparticle of claim 1, wherein said copolymer shell covers at least about 80 percent of said metallic core.

16. The nanoparticle of claim 1, wherein said copolymer shell covers at least about 90 percent of said metallic core.

17. The nanoparticle of claim 1, further comprising an imaging or therapeutic moiety attached to said copolymer shell.

18. The nanoparticle of claim 1, further comprising an imaging or therapeutic moiety that forms an ionic complex with said nanoparticle.

19. The nanoparticle of claim 18, wherein said therapeutic moiety is a short negatively charged oligonucleotide or oligonucleotide duplex.

* * * * *